(12) United States Patent
Lam

(10) Patent No.: US 8,854,138 B2
(45) Date of Patent: Oct. 7, 2014

(54) BUFFER AMPLIFIER

(71) Applicant: Chi Ming John Lam, Shatin (HK)

(72) Inventor: Chi Ming John Lam, Shatin (HK)

(*) Notice: Subject to any disclaimer, the term of this patent is extended or adjusted under 35 U.S.C. 154(b) by 0 days.

(21) Appl. No.: 13/692,703

(22) Filed: Dec. 3, 2012

(65) Prior Publication Data

US 2013/0093517 A1     Apr. 18, 2013

(51) Int. Cl.
```
H03F 3/217      (2006.01)
A61K 31/4045    (2006.01)
A23L 1/30       (2006.01)
A23L 1/302      (2006.01)
A23L 1/305      (2006.01)
A61K 31/519     (2006.01)
H03F 3/45       (2006.01)
A61K 31/205     (2006.01)
A61K 31/675     (2006.01)
A61K 31/198     (2006.01)
A61K 31/40      (2006.01)
A61K 31/4415    (2006.01)
A61K 31/405     (2006.01)
A61K 31/714     (2006.01)
A61K 31/7056    (2006.01)
```
(52) U.S. Cl.
CPC ........ *H03F 3/45071* (2013.01); *A61K 31/4045* (2013.01); *A23L 1/30* (2013.01); *A23L 1/302* (2013.01); *A23L 1/305* (2013.01); *A61K 31/519* (2013.01); *A61K 31/205* (2013.01); *A61K 31/675* (2013.01); *A61K 31/198* (2013.01); *A61K 31/40* (2013.01); *A61K 31/4415* (2013.01); *A61K 31/405* (2013.01); *A61K 31/714* (2013.01); *A23V 2002/00* (2013.01); *A61K 31/7056* (2013.01)
USPC .......................................... 330/264; 330/255

(58) Field of Classification Search
CPC ........................................................ H03F 3/217
USPC .......................................... 330/264, 255, 269
See application file for complete search history.

(56) References Cited

U.S. PATENT DOCUMENTS

| | | | | |
|---|---|---|---|---|
| 3,914,702 | A | * | 10/1975 | Gehweiler .................... 330/264 |
| 4,021,747 | A | * | 5/1977 | Todokoro ..................... 330/253 |
| 4,433,303 | A | * | 2/1984 | Sasaki ............................ 330/264 |
| 6,411,167 | B2 | * | 6/2002 | Laaser ........................... 330/264 |
| 7,920,027 | B2 | * | 4/2011 | Keerti ............................ 330/264 |

* cited by examiner

*Primary Examiner* — Henry Choe
(74) *Attorney, Agent, or Firm* — William J. Sapone; Ware Fressola Maguire & Barber LLP

(57) ABSTRACT

A buffer amplifier with unity voltage gain, high input impedance, high speed, high current gain, high output power and low offset includes three stages and a DC servo circuit. The first stage of the buffer amplifier contains complementary N-channel and P-channel MOSFET source followers that provide high input impedance to buffer the input signal source. A feedback DC servo signal is provided to correct the subsequent stages so as to maintain the output at virtual DC ground level. The second stage is a driver stage that also contains complementary N-channel and P-channel MOSFET source followers to provide sufficient current to drive the output stage. The last stage is an output stage that contains at least one pair of complementary power MOSFETs or BJTs to deliver high currents to a load.

28 Claims, 4 Drawing Sheets

BUFFER AMPLIFIER

TECHNICAL FIELD

This invention relates to an amplifier, and in particular a buffer amplifier.

BACKGROUND OF THE INVENTION

Buffer amplifiers can be found in many applications that require boosting output current without affecting the speed and bandwidth while maintaining the same voltage gain.

SUMMARY OF THE INVENTION

According to the present invention, there is provided a buffer amplifier including at least a first stage, a driver stage and an output stage, wherein said first stage includes a first N-channel metal-oxide-semiconductor field-effect transistor (MOSFET) and a first P-channel MOSFET forming a first pair of complementary MOSFETs, wherein each of said first N-channel MOSFET and said first P-channel MOSFET includes respectively a source, a drain and a gate, wherein said first stage includes a second N-channel MOSFET and a second P-channel MOSFET forming a second pair of complementary MOSFETs, wherein each of said second N-channel MOSFET and said second P-channel MOSFET includes respectively a source, a drain and a gate, and wherein said first pair of complementary MOSFETs form a first pair of source followers.

BRIEF DESCRIPTION OF THE DRAWINGS

Embodiments of the present invention will now be described, by way of examples only, with reference to the accompanying drawings, in which.

DETAILED DESCRIPTION OF THE PREFERRED EMBODIMENT[S]

For a buffer amplifier according to the present invention, the input and output are maintained at virtual DC ground level so that no coupling capacitors are needed. Therefore, the buffer amplifier has a wide bandwidth and it can amplify low frequency signals down to DC. The output current of the buffer amplifier can easily go beyond 10 A to 50 A. Any desired output current can be achieved by paralleling pairs of complementary power transistors in the output stage, to be discussed below. In addition, the buffer amplifier is stable with, or without, global feedback loop enclosing it.

Figure 1:
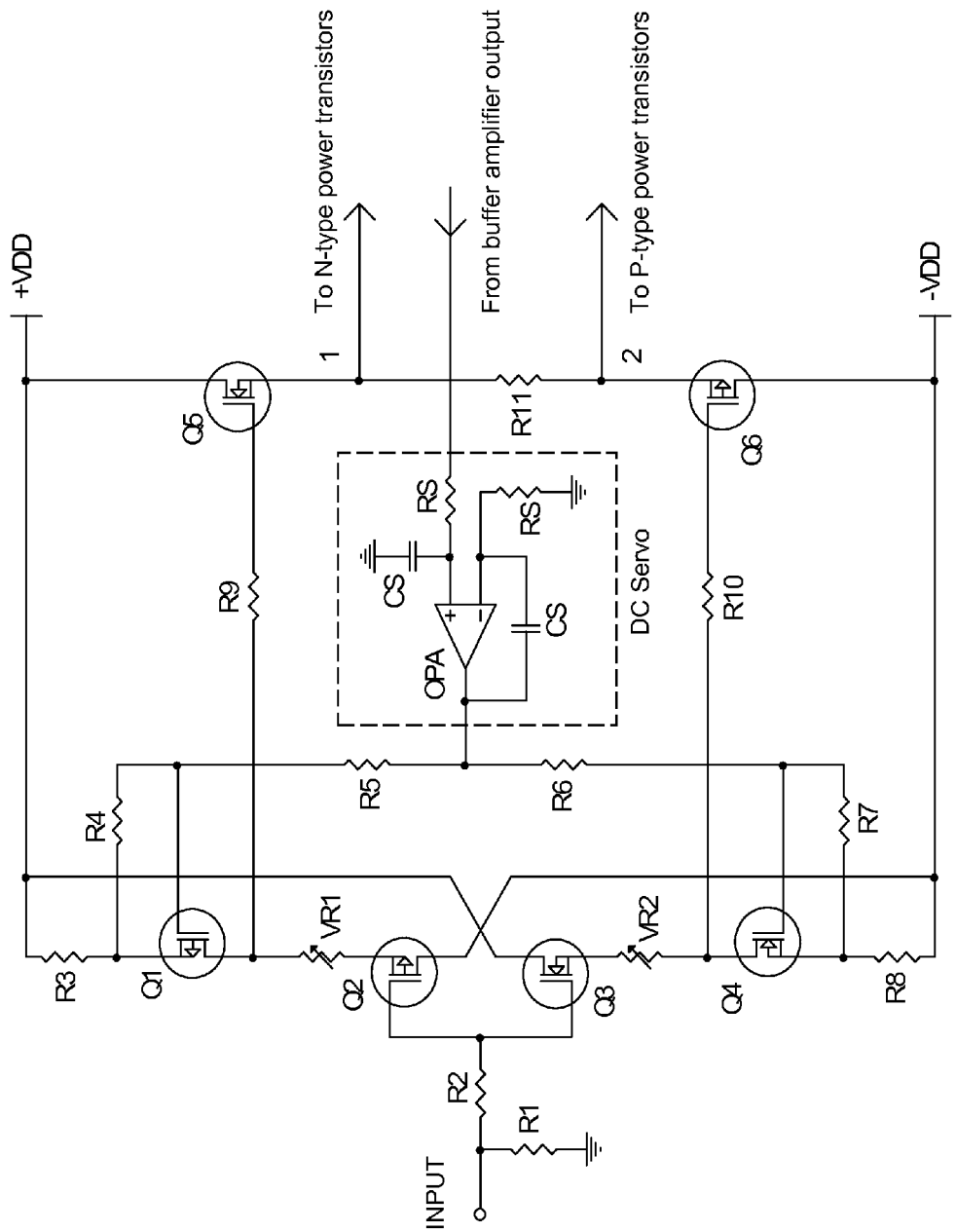
FIG. 1 shows a circuit diagram of the a first stage and a second stage of a buffer amplifier according to a first embodiment of the present invention.

FIG. 1 shows a first stage and a second stage of a buffer amplifier according to a first embodiment of the present invention. It can be seen that the first stage includes a P-channel metal-oxide-semiconductor field-effect transistor (MOSFET) Q2 and an N-channel MOSFET Q3 which are complementary with each other, and collectively forming a pair of source followers. The outputs of the source followers Q2, Q3 are connected to drains of two complementary MOSFETs Q1 (being a P-channel MOSFET), Q4 (being an N-channel MOSFET) respectively. MOSFETs Q1, Q4 are used as active load for the source followers Q2, Q3 to improve linearity and to set up a DC quiescent current. Gates of Q1, Q4 are connected together via resistors R5, R6 which are of identical value and connected with each other in series. The junction between resistors R5, R6 is connected to an output of a DC servo that monitors the DC level of the buffer amplifier output.

If the buffer amplifier output drifts away from the DC ground level, it will cause the DC quiescent point at the junction between resistors R5, R6 to change accordingly. This affects the DC quiescent biasing of the first and second stage. The second stage (which is also the driver stage) also includes two MOSFETs Q5 (being an N-channel MOSFET), Q6 (being a P-channel MOSFET) which are complementary with each other and act as a pair of source followers in that the two sources are connected together by resistor R11. The DC servo loop works in such a way that a drift of DC level in the buffer amplifier output will affect the quiescent points of the first and second stages in such a way that it opposes the drift. Thus, the use of a DC servo circuit will maintain the output of the buffer amplifier at a virtual DC ground level at all time.

Each of the MOSFETs Q1, Q2, Q3, Q4 includes respectively a source, a drain and a gate. As mentioned above, the pair of complementary MOSFETs Q2, Q3 form a pair of source followers. The gate of the N-channel MOSFET Q3 and the gate of the P-channel MOSFET Q2 are connected together. Input signals may be fed to the gates of the MOSFETs Q2, Q3 through a gate stopper resistor R2. A further resistor R1 is connected between an input of the amplifier and a ground.

The drain of the P-channel MOSFET Q2 is connected to a negative power supply −VDD and the drain of the N-channel MOSFET Q3 is connected to a positive power supply +VDD.

The source of the P-channel MOSFET Q2 is connected to the drain of the P-channel MOSFET Q1 through a variable resistor VR1. The source of the P-channel MOSFET Q1 is connected to the positive power supply +VDD through a resistor R3. A resistor R4 is connected between the gate and the source of the P-channel MOSFET Q1.

The source of the N-channel MOSFET Q3 is connected to the drain of the N-channel MOSFET Q4 through a variable resistor VR2. The source of the N-channel MOSFET Q4 is connected to the negative power supply −VDD through a resistor R8. A resistor R7 is connected between the gate and the source of the N-channel MOSFET Q4. The gate of the P-channel MOSFET Q1 is connected to the gate of the N-channel MOSFET Q4 through resistors R5, R6 in series connection.

The buffer amplifier includes a N-channel MOSFET Q5 with a source, a drain and a gate. The drain of the P-channel MOSFET Q1 is connected to the gate of the N-channel MOSFET Q5 through a gate stopper resistor R9. The buffer amplifier also includes a P-channel MOSFET Q6 with a source, a drain and a gate. The drain of the N-channel MOSFET Q4 is connected to the gate of the P-channel MOSFET Q6 through a gate stopper resistor R10. The source of the N-channel MOSFET Q5 is connected to the source of the P-channel MOSFET Q6 through a resistor R11. The N-channel MOSFET Q5 and P-channel MOSFET Q6 form a pair of source followers, and form the driver stage (second stage) of the buffer amplifier.

Figure 2:
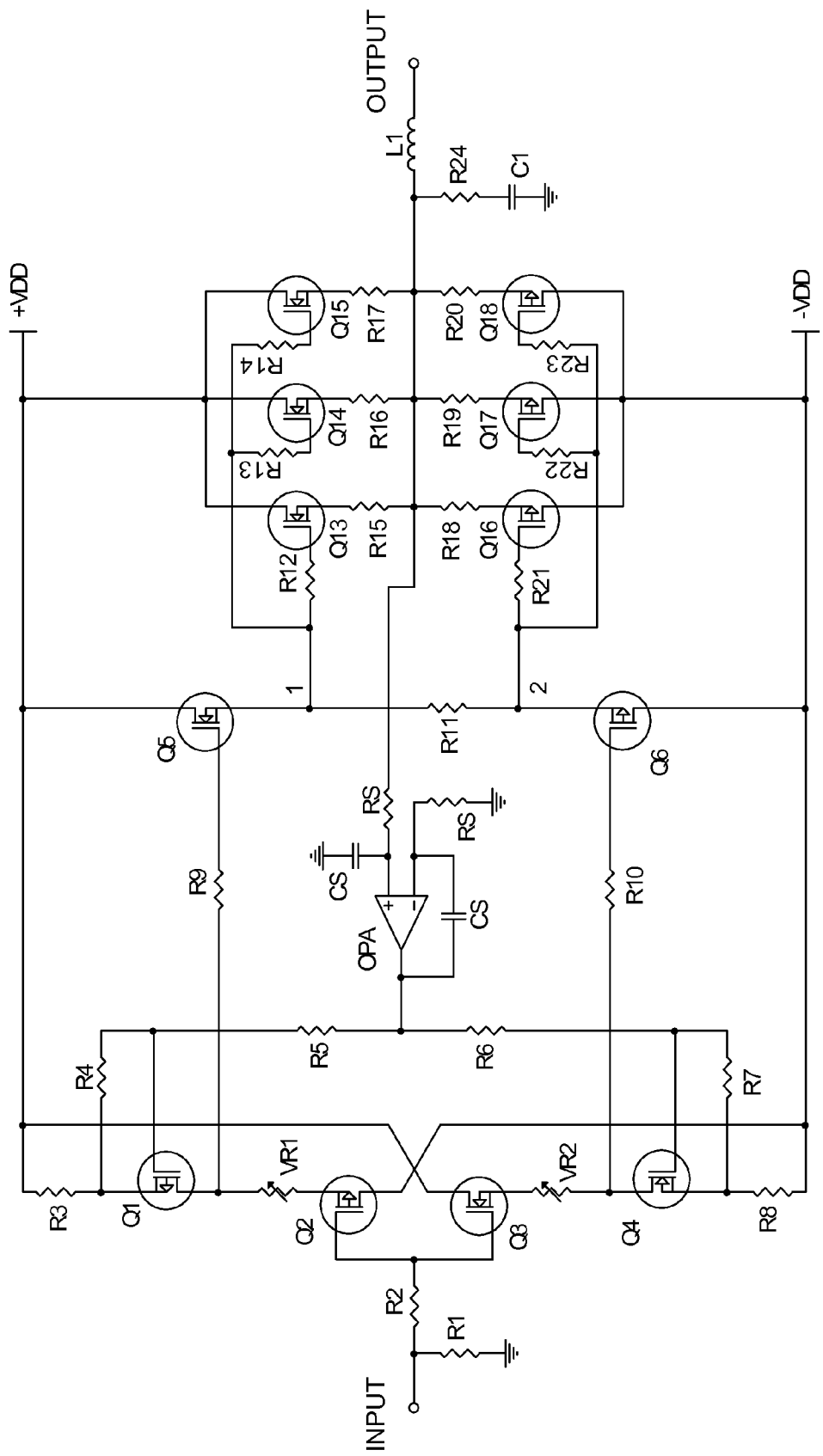
FIG. 2 shows a circuit diagram of a complete buffer amplifier according to a second embodiment of the present invention, being a modified arrangement of the arrangement shown in FIG. 1, in which power metal-oxide-semiconductor field-effect transistors (MOSFETs) are used in an output stage.

FIG. 2 shows a complete buffer amplifier according to the present invention that employs the arrangement of FIG. 1 and complementary power MOSFETs in the output stage. Three pairs of power MOSFETs Q13, Q16; Q14, Q17; Q15, Q18 are shown in FIG. 2. If a greater output current is needed, more power MOSFETs can be connected in parallel. Resistors R12, R13, R14 and R21, R22, R23 are gate stopper resistors for preventing the power MOSFETs from parasitic oscillations. A simple output filter consisting of L1, R24 and C1 further prevents parasitic oscillations from the buffer amplifier.

The source of the N-channel MOSFET Q5 is connected to a gate of the N-channel power MOSFET Q13 through the gate stopper resistor R12. The source of the third P-channel MOSFET Q5 is connected to a gate of the P-channel power MOSFET Q16 through the gate stopper resistor R21. A drain of the N-channel power MOSFET Q13 is connected to the positive power supply +VDD. A drain of the P-channel power MOSFET Q16 is connected to the negative power supply –VDD. A source of the N-channel power MOSFET Q13 is connected to a source of the P-channel power MOSFET Q16 through resistors R15, R18 in series connection. The junction between the resistors R15, R18 is the output of the buffer amplifier.

Additional pairs of complementary power MOSFETs Q14, Q17; Q15, Q18 are connected in parallel to the output stage to boost output current. The output is connected to a non-inverting input of a DC servo circuit, and an output of the DC servo circuit is fed to the junction between the resistor R5 and the resistor R6.

Figure 3:
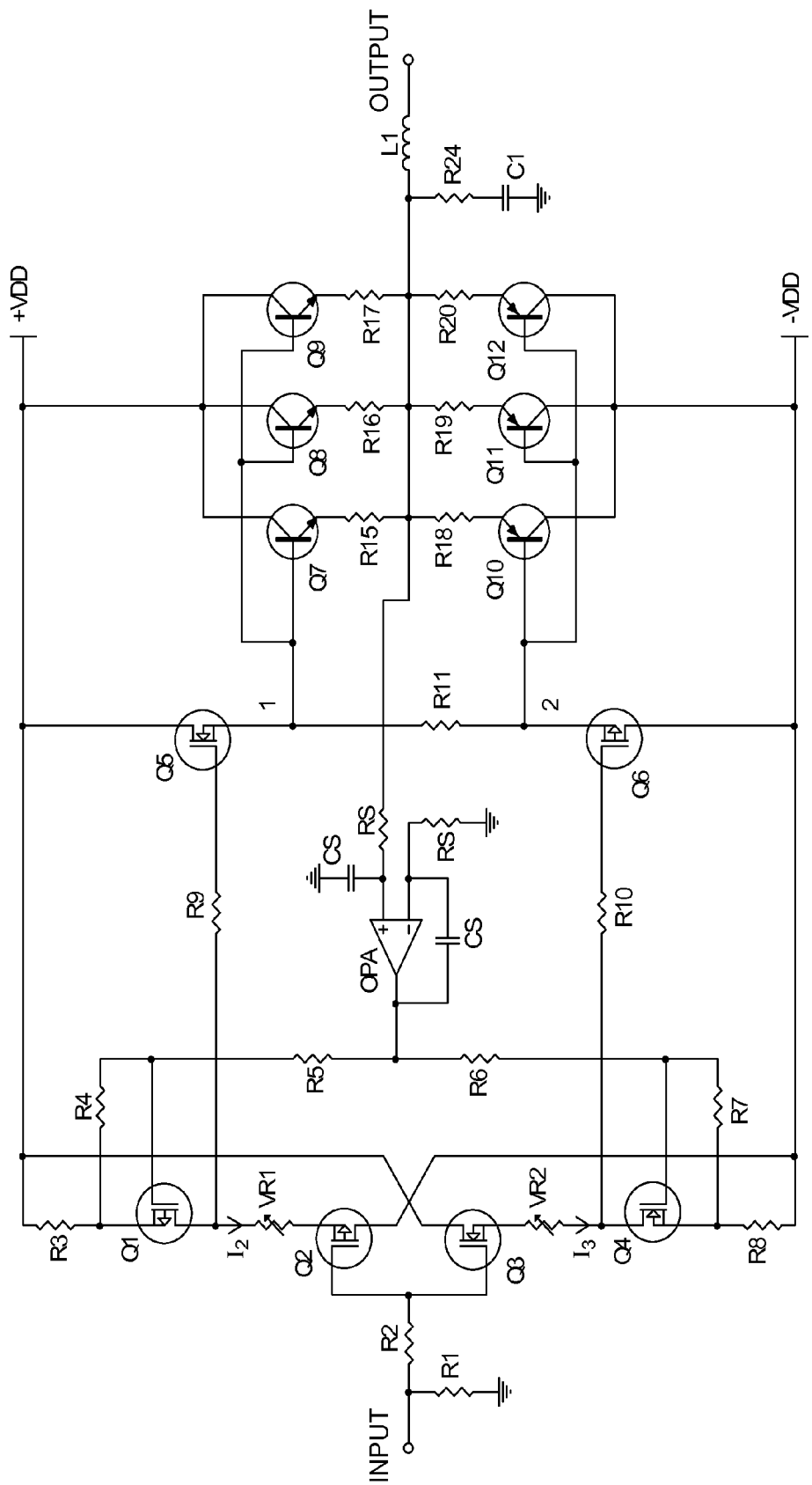
FIG. 3 shows a circuit diagram of a complete buffer amplifier according to a third embodiment of the present invention, being a further modified arrangement of the arrangement shown in FIG. 1, in which power bipolar junction transistors (BJTs) are used in an output stage.

FIG. 3 shows a complete buffer amplifier according to a further embodiment of the present invention that employs the arrangement of FIG. 1 and complementary power bipolar junction transistors (BJTs). Since BJTs are used, gate stopper resistors can be eliminated.

The source of the N-channel MOSFET Q5 is connected to a base of a NPN power transistor Q7. The source of the P-channel MOSFET Q6 is connected to a base of a PNP power transistor Q10. A collector of the NPN power transistor Q7 is connected to a positive power supply +VDD, and a collector of the PNP power transistor Q10 is connected to a negative power supply –VDD. An emitter of the NPN power transistor Q7 is connected to an emitter of the PNP power transistor Q10 through resistors R15, R18 in series connection. The junction between the resistors R15, R18 is the output of the buffer amplifier.

Further pairs of complementary power bipolar junction transistors (BJTs) Q8, Q11; Q9, Q12 are connected in parallel to the output stage to boost output current. The output is connected to a non-inverting input of a DC servo circuit, and the output of the DC servo circuit is fed to the junction between resistors R5, R6.

Figure 4:
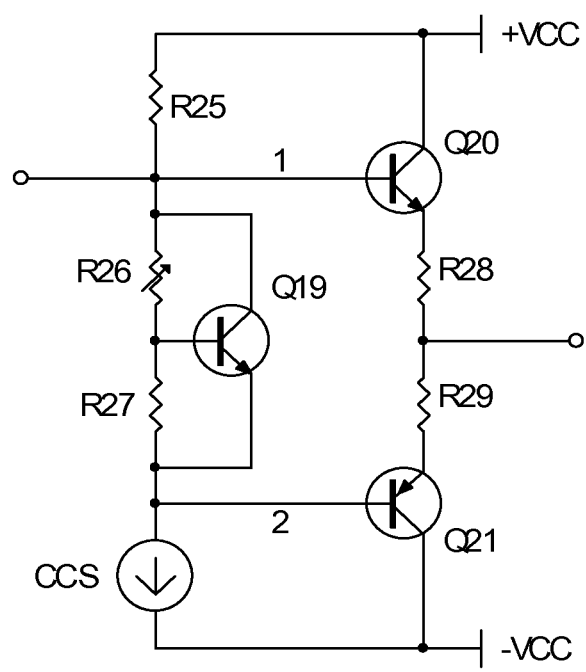
FIG. 4 shows a circuit diagram of a pair of power BJTs and a $V_{BE}$ multiplier formed by a BJT and two resistors for setting the quiescent current, which may be used in the buffer amplifier of FIGS. 2 and 3.

In order to minimize crossover distortion, proper quiescent current must be set for the power transistors in the output stage. In a conventional power amplifier, a medium power BJT is often used to operate as a so-called "$V_{BE}$ multiplier" to bias the power transistors in class-AB or class-A with proper quiescent current. FIG. 4 shows a typical $V_{BE}$ multiplier with a pair of BJT power transistors Q20, Q21. Resistor R26 (which may be a variable resistor) is used to adjust the DC potential different between points 1 and 2. The DC potential difference between points 1 and 2 is governed by:

$$V_{12} = V_{BE} \times \left(1 + \frac{R26}{R27}\right)$$

where $V_{BE}$ is the voltage between the base and emitter of transistor Q19. $V_{12}$ is adjusted in such a way that it is slightly higher than the sum of $V_{BE}$ of Q20 and $V_{BE}$ of Q21. As a general property of BJT transistor, $V_{BE}$ has a negative temperature coefficient such that $|V_{BE}|$ decreases when temperature rises. Transistor Q19 is mounted in the same heat-sink with transistors Q20, Q21 in order to catch the same temperature rise. Since $V_{12}$ is proportional to $V_{BE}$, it will also decrease when temperature rises. Hence, the decreased $V_{12}$ reduces the quiescent current in power transistors Q20, Q21 and prevents the thermal run-away problem. In addition, it should be noted that global negative feedback is usually needed to apply to the output in FIG. 4 so that the output can be maintained at virtual DC ground level.

For the buffer amplifiers in FIGS. 1 to 3, a $V_{BE}$ multiplier is not required because a different technique is used. This technique is illustrated in FIG. 3. The goal is to set up a proper DC potential difference between the points 1 and 2, i.e., the bases of the power transistors. Let $V_{12}$ denote the DC potential difference between points 1 and 2 in FIG. 3. As there is no current flowing at the gate of a MOSFET, it can be easily seen that:

$$V_{12}=(I_2 \times VR1+V_{SG2})+(I_3 \times VR2+V_{GS3})-(V_{GS5}+V_{SG6}) \quad \text{Equation (1)}$$

where
$I_2$=source current in Q2;
$I_3$=source current in Q3;
$V_{SG2}$=DC voltage across the source and gate of Q2;
$V_{GS3}$=DC voltage across the gate and source of Q3;
$V_{GS5}$=DC voltage across the gate and source of Q5; and
$V_{SG6}$=DC voltage across the source and gate of Q6.

Variable resistors VR1 and VR2 are used to adjust the desire $V_{12}$ so as to set quiescent current for the output power transistors. MOSFETs Q5, Q6 are mounted in the same heat-sink with power transistors Q7, Q8, Q9, Q10, Q11, Q12. However, MOSFETs Q1, Q2, Q3, Q4 are not mounted in the same heat-sink. Therefore, $I_2$, $V_{SG2}$, $I_3$ and $V_{GS3}$ are not affected by the temperature change in transistors Q7, Q8, Q9, Q10, Q11, Q12. Thus the first two terms in Equation (1), i.e., ($I_2 \times VR1+V_{SG2}$) and ($I_3 \times VR2+V_{GS3}$), remain constant.

On the other hand, since MOSFETs Q5, Q6 are mounted in the same heat-sink, these two MOSFETs will closely resemble the temperature of the power transistors Q7, Q8, Q9, Q10, Q11, Q12. As a general property of a MOSFET, $V_{GS}$ has a positive temperature coefficient such that $|V_{GS}|$ increases when temperature rises. Additionally, it should be noted that $V_{GS}$ is a positive value for N-channel MOSFET and a negative value for P-channel MOSFET. The value of the third term in Equation (1), namely ($V_{GS5}+V_{SG6}$), is therefore a positive figure because MOSFET Q5 is an N-channel and MOSFET Q6 is a P-channel MOSFET. For instance, if $V_{GS5}$=1.9V and $V_{GS6}$=−2.1V for a given temperature, then $$V_{GS5} + V_{SG6} = V_{GS5} - V_{GS6}$$
$$= 1.9 \text{ V} - (-2.1 \text{ V})$$
$$= 4 \text{ V}$$

Thus, the value of the third term in Equation (1), namely ($V_{GS5}+V_{SG6}$), increases when temperature rises. Hence the overall $V_{12}$ decreases while temperature rises. It is because the first two terms in Equation (1) remain constant while the value of the third term increases when temperature rises. As a result, the decreased $V_{12}$ will reduce the quiescent current in Q7, Q8, Q9, Q10, Q11, Q12 and prevents the power transistors from thermal run-away in case of a rise in temperature.

It can be seen that a buffer amplifier according to the present invention has unity voltage gain, high input impedance, high speed, high current gain, high output power and low offset. Such a buffer amplifier comprises of three stages and a DC servo circuit. The first stage of the buffer amplifier includes complementary N-channel and P-channel MOSFET source followers that provide high input impedance to buffer the input signal source. It also takes the DC servo signal to correct the subsequent stages so as to maintain the output at virtual DC ground level. The second stage is a driver that also contains complementary N-channel and P-channel MOSFET source followers to provide sufficient current to drive the output stage. The output stage includes at least one pair of complementary power MOSFETs or BJTs to deliver high currents to a load.

Referring to the DC servo circuit shown in FIGS. 1, 2 and 3 and discussed above, it can be seen that such includes an operational amplifier OPA, two resistors RS, RS, and two capacitors CS, CS. The operational amplifier OPA includes a non-inverting input, an inverting input and an output. The operational amplifier OPA is powered by dual DC power supplies. One of the capacitors CS is connected between the non-inverting input of the operational amplifier OPA and the ground. The other of the capacitors CS is connected between the inverting input of the operational amplifier OPA and the output of the operational amplifier OPA. A first end of one of the resistors RS is connected to the non-inverting input of the operational amplifier OPA and a second end of this resistor RS is connected to the output of the buffer amplifier. The other of the resistors RS is connected between the inverting input of the operational amplifier OPA and the ground.

It should be understood that the above only illustrates examples whereby the present invention may be carried out, and that various modifications and/or alterations may be made thereto without departing from the spirit of the invention.

It should also be understood that certain features of the invention, which are, for clarity, described in the context of separate embodiments, may be provided in combination in a single embodiment. Conversely, various features of the invention that are, for brevity, described in the context of a single embodiment, may also be provided separately or in any appropriate sub-combinations.

The invention claimed is:

1. A buffer amplifier comprising:
at least a first stage, a driver stage and an output stage,
wherein said first stage includes a first N-channel metal-oxide-semiconductor field-effect transistor (MOSFET) and a first P-channel MOSFET forming a first pair of complementary MOSFETs,
wherein each of said first N-channel MOSFET and said first P-channel MOSFET includes respectively a source, a drain and a gate,
wherein said first stage includes a second N-channel MOSFET and a second P-channel MOSFET forming a second pair of complementary MOSFETs,
wherein each of said second N-channel MOSFET and said second P-channel MOSFET includes respectively a source, a drain and a gate, and
wherein said first pair of complementary MOSFETs form a first pair of source followers; and,
wherein said gate of said first N-channel MOSFET and said gate of said first P-channel MOSFET are connected together, wherein an input signal is adapted to be fed to said gates of said first pair of complementary MOSFETs through a first resistor which acts as a gate stopper resistor, and wherein a second resistor is connected between an input of said buffer amplifier and a ground.

2. The buffer amplifier according to claim 1 wherein said drain of said first P-channel MOSFET is connected to a negative power supply, and wherein said drain of said first N-channel MOSFET is connected to a positive power supply.

3. A buffer amplifier comprising:
at least a first stage, a driver stage and an output stage,
wherein said first stage includes a first N-channel metal-oxide-semiconductor field-effect transistor (MOSFET) and a first P-channel MOSFET forming a first pair of complementary MOSFETs,
wherein each of said first N-channel MOSFET and said first P-channel MOSFET includes respectively a source, a drain and a gate,
wherein said first stage includes a second N-channel MOSFET and a second P-channel MOSFET forming a second pair of complementary MOSFETs,
wherein each of said second N-channel MOSFET and said second P-channel MOSFET includes respectively a source, a drain and a gate,
wherein said first pair of complementary MOSFETs form a first pair of source followers,
wherein said drain of said first P-channel MOSFET is connected to a negative power supply, and wherein said drain of said first N-channel MOSFET is connected to a positive power supply, and,
wherein said source of said first P-channel MOSFET is connected to said drain of said second P-channel MOSFET through a first variable resistor, wherein said source of said second P-channel MOSFET is connected to the positive power supply through a third resistor, and a fourth resistor is connected between said gate and said source of said second P-channel MOSFET.

4. The buffer amplifier according to claim 2 wherein said source of said first N-channel MOSFET is connected to said drain of said second N-channel MOSFET through a second variable resistor, wherein said source of said second N-channel MOSFET is connected to the negative power supply through a fifth resistor, and wherein a sixth resistor is connected between said gate and said source of said second N-channel MOSFET.

5. The buffer amplifier according to claim 3 wherein said gate of said second P-channel MOSFET is connected to said gate of said second N-channel MOSFET through a seventh resistor and an eighth resistor in series connection.

6. The buffer amplifier according to claim 3 further comprising a third N-channel MOSFET with a source, a drain and a gate, wherein said drain of said second P-channel MOSFET is connected to said gate of said third N-channel MOSFET through a ninth resistor which acts as a gate stopper resistor.

7. The buffer amplifier according to claim 4 further comprising a third P-channel MOSFET with a source, a drain and a gate, wherein said drain of said second N-channel MOSFET is connected to said gate of said third P-channel MOSFET through a tenth resistor which acts as a gate stopper resistor.

8. The buffer amplifier according to claim 7 wherein said third P-channel MOSFET and said N-channel MOSFET form a second pair of source followers.

9. The buffer amplifier according to claim 6 wherein said source of said third N-channel MOSFET is connected to said source of said third P-channel MOSFET through an eleventh resistor.

10. The buffer amplifier according to claim 8 wherein said third N-channel MOSFET and said third P-channel MOSFET form said driver stage.

11. The buffer amplifier according to claim 10 wherein said source of said third N-channel MOSFET is connected to a gate of an N-channel power MOSFET through a twelfth resistor which acts as a gate stopper resistor, wherein said source of said third P-channel MOSFET is connected to a gate of a P-channel power MOSFET through a thirteenth resistor which acts as a gate stopper resistor, wherein a drain of said N-channel power MOSFET is connected to the positive power supply, wherein a drain of said P-channel power MOSFET is connected to the negative power supply, wherein a source of said N-channel power MOSFET is connected to a source of said P-channel power MOSFET through a fourteenth resistor and a fifteenth resistor in series connection, wherein said N-channel power MOSFET and said P-channel power MOSFET are complementary with each other, and wherein the junction between said fourteenth resistor and fifteenth resistor is the output of said buffer amplifier.

12. The buffer amplifier according to claim 11 wherein at least a further pair of complementary power MOSFETs are connected in parallel to the output stage.

13. The buffer amplifier according to claim 11 wherein the output is connected to a non-inverting input of a DC servo circuit, and wherein an output of said DC servo circuit is fed to the junction between said seventh resistor and said eighth resistor.

14. The buffer amplifier according to claim 10 wherein said source of said third N-channel MOSFET is connected to a base of a NPN power transistor, wherein said source of said third P-channel MOSFET is connected to a base of a PNP power transistor, wherein a collector of said NPN power transistor is connected to the positive power supply, wherein a collector of said PNP power transistor is connected to the negative power supply, wherein an emitter of said NPN power transistor is connected to an emitter of said PNP power transistor through a sixteenth resistor and seventeenth resistor in series connection, wherein said NPN power transistor and said PNP transistor are complementary with each other, and wherein the junction between said sixteenth resistor and said seventeenth resistor is the output of said buffer amplifier.

15. The buffer amplifier according to claim 14 wherein at least a further pair of complementary power bipolar junction transistors (BJTs) are connected in parallel to said output stage.

16. The buffer amplifier according to claim 14 wherein said output is connected to a non-inverting input of a DC servo circuit, and wherein said output of said DC servo circuit is fed to the junction between said seventh resistor and said eighth resistor.

17. The buffer amplifier according to claim 13 wherein said DC servo circuit includes an operational amplifier, an eighteenth resistor, a nineteenth resistor, a first capacitor and a second capacitor,
  wherein said operational amplifier includes a non-inverting input, an inverting input and an output,
  wherein said operational amplifier is powered by dual DC power supplies,
  wherein said first capacitor is connected between said non-inverting input of said operational amplifier and a ground,
  wherein said second capacitor is connected between said inverting input of said operational amplifier and said output of said operational amplifier,
  wherein a first end of said eighteenth resistor is connected to said non-inverting input of said operational amplifier and a second end of said first resistor is connected to said output of said buffer amplifier, and
  wherein said nineteenth resistor is connected between said inverting input of said operational amplifier and said ground.

18. The buffer amplifier according to claim 16 wherein said DC servo circuit includes an operational amplifier, an eighteenth resistor, a nineteenth resistor, a first capacitor and a second capacitor,
  wherein said operational amplifier includes a non-inverting input, an inverting input and an output,
  wherein said operational amplifier is powered by dual DC power supplies,
  wherein said first capacitor is connected between said non-inverting input of said operational amplifier and a ground,
  wherein said second capacitor is connected between said inverting input of said operational amplifier and said output of said operational amplifier,
  wherein a first end of said eighteenth resistor is connected to said non-inverting input of said operational amplifier and a second end of said first resistor is connected to said output of said buffer amplifier, and
  wherein said nineteenth resistor is connected between said inverting input of said operational amplifier and said ground.

19. The buffer amplifier according to claim 3 wherein said source of said first N-channel MOSFET is connected to said drain of said second N-channel MOSFET through a second variable resistor, wherein said source of said second N-channel MOSFET is connected to the negative power supply through a fifth resistor, and wherein a sixth resistor is connected between said gate and said source of said second N-channel MOSFET.

20. The buffer amplifier according to claim 19 further comprising a third P-channel MOSFET with a source, a drain and a gate, wherein said drain of said second N-channel MOSFET is connected to said gate of said third P-channel MOSFET through a tenth resistor which acts as a gate stopper resistor.

21. The buffer amplifier according to claim 20 wherein said third P-channel MOSFET and said N-channel MOSFET form a second pair of source followers.

22. The buffer amplifier according to claim 21 wherein said third N-channel MOSFET and said third P-channel MOSFET form said driver stage.

23. The buffer amplifier according to claim 22 wherein said source of said third N-channel MOSFET is connected to a gate of an N-channel power MOSFET through a twelfth resistor which acts as a gate stopper resistor, wherein said source of said third P-channel MOSFET is connected to a gate of a P-channel power MOSFET through a thirteenth resistor which acts as a gate stopper resistor, wherein a drain of said N-channel power MOSFET is connected to the positive power supply, wherein a drain of said P-channel power MOSFET is connected to the negative power supply, wherein a source of said N-channel power MOSFET is connected to a source of said P-channel power MOSFET through a fourteenth resistor and a fifteenth resistor in series connection, wherein said N-channel power MOSFET and said P-channel power MOSFET are complementary with each other, and wherein the junction between said fourteenth resistor and fifteenth resistor is the output of said buffer amplifier.

24. The buffer amplifier according to claim 23 wherein at least a further pair of complementary power MOSFETs are connected in parallel to the output stage.

25. The buffer amplifier according to claim 23 wherein the output is connected to a non-inverting input of a DC servo circuit, and wherein an output of said DC servo circuit is fed to the junction between said seventh resistor and said eighth resistor.

26. The buffer amplifier according to claim 22 wherein said source of said third N-channel MOSFET is connected to a base of a NPN power transistor, wherein said source of said third P-channel MOSFET is connected to a base of a PNP power transistor, wherein a collector of said NPN power transistor is connected to the positive power supply, wherein a collector of said PNP power transistor is connected to the negative power supply, wherein an emitter of said NPN power transistor is connected to an emitter of said PNP power transistor through a sixteenth resistor and seventeenth resistor in series connection, wherein said NPN power transistor and said PNP transistor are complementary with each other, and wherein the junction between said sixteenth resistor and said seventeenth resistor is the output of said buffer amplifier.

27. The buffer amplifier according to claim 26 wherein at least a further pair of complementary power bipolar junction transistors (BJTs) are connected in parallel to said output stage.

28. The buffer amplifier according to claim 26 wherein said output is connected to a non-inverting input of a DC servo circuit, and wherein said output of said DC servo circuit is fed to the junction between said seventh resistor and said eighth resistor.

* * * * *